(12) United States Patent
Chen et al.

(10) Patent No.: US 6,624,165 B2
(45) Date of Patent: Sep. 23, 2003

(54) CYCLOPENTENE DERIVATIVES USEFUL AS ANTAGONISTS OF THE MOTILIN RECEPTOR

(75) Inventors: Robert H. Chen, Belle Mead, NJ (US); Min A. Xiang, Bridgewater, NJ (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 10/119,255

(22) Filed: Apr. 9, 2002

(65) Prior Publication Data

US 2002/0111484 A1 Aug. 15, 2002

Related U.S. Application Data

(62) Division of application No. 09/803,605, filed on Mar. 9, 2001, now Pat. No. 6,392,040.
(60) Provisional application No. 60/188,917, filed on Mar. 13, 2000.

(51) Int. Cl.[7] .................... C07D 417/10; C07D 413/10; A61K 31/5375

(52) U.S. Cl. ................ 514/236.2; 544/134; 544/367; 546/209; 514/254.03; 514/326

(58) Field of Search ................ 544/367, 134; 546/209; 514/236.2, 254.03, 326

(56) References Cited

U.S. PATENT DOCUMENTS

| | | | |
|---|---|---|---|
| 5,086,053 A | 2/1992 | Brodin et al. | |
| 5,824,678 A | 10/1998 | Harrison et al. | |
| 5,972,939 A | * 10/1999 | Chen et al. | 514/237.8 |

OTHER PUBLICATIONS

Search Report from corresponding PCT Application No. WO 01/68620 A1.

* cited by examiner

*Primary Examiner*—Joseph K. McKane
*Assistant Examiner*—Golam M. M. Shameem

(57) ABSTRACT

The compounds of formula I are useful in treating gastrointestinal disorders associated with antagonizing the motilin receptor. The compounds compete with erythromycin and motilin for the motilin receptor. In addition the compounds are antagonists of the contractile smooth muscle response to those ligands.

11 Claims, No Drawings

CYCLOPENTENE DERIVATIVES USEFUL AS ANTAGONISTS OF THE MOTILIN RECEPTOR

This application is a division of application Ser. No. 09/803,605 U.S. Pat. No. 6,392,060, filed on Mar. 9, 2001, and claims the benefit of provisional application No. 60/188,917, filed Mar. 13, 2000.

FIELD OF THE INVENTION

This invention relates to a series of novel cyclopentene derivatives, pharmaceutical compositions containing them and intermediates used in their manufacture. The compounds of the invention are useful as non-peptidyl antagonists of the motilin receptor. In addition, the compounds display efficacy and potency which are comparable to known motilin and erythromycin antagonists.

BACKGROUND

In mammals, the digestion of nutrients and the elimination of waste is controlled by the gastrointestinal system. This system is, to say the least, complicated. There are a number of natural peptides, ligands, enzymes, and receptors which play a vital role in this system and are potential targets for drug discovery. Modifying the production of, or responses to these endogenous substances can have an effect upon the physiological responses such as diarrhea, nausea, and abdominal cramping. One example of an endogenous substance which affects the gastrointestinal system is motilin.

Motilin is a peptide of 22 amino acids which is produced in the gastrointestinal system of a number of species. Although the sequence of the peptide varies from species to species, there are a great deal of similarities. For example, human motilin and porcine motilin are identical; while motilin isolated from the dog and the rabbit differ by five and four amino acids, respectively. Motilin induces smooth muscle contractions in the stomach tissue of dogs, rabbits, and humans as well as in the colon of rabbits. Apart from local gastrointestinal intestinal tissues, motilin and its receptors have been found in other tissues. For example, motilin has been found in circulating plasma, where a rise in the concentration of motilin has been associated with gastric effects which occur during fasting in dogs and humans. Itoh, Z. et al. Scand. *J. Gastroenterol.* 11:93–110, (1976); Vantrappen, G. et al. *Dig. Dis Sci* 24, 497–500 (1979). In addition, when motilin was intravenously administered to humans it was found to increase gastric emptying and gut hormone release. Christofides, N. D. et al. *Gastroenterology* 76:903–907, 1979.

Aside from motilin itself, there are other substances which are agonists of the motilin receptor and which elicit gastrointestinal emptying. One of those agents is the antibiotic erythromycin. Even though erythromycin is a useful drug, a great number of patients are affected by the drug's gastrointestinal side effects. Studies have shown that erythromycin elicits biological responses that are comparable to motilin itself and therefore may be useful in the treatment of diseases such as chronic idiopathic intestinal pseudo-obstruction and gastroparesis. Weber, F. et al., *The American Journal of Gastroenterology*, 88:4, 485–90 (1993).

Although motilin and erythromycin are agonists of the motilin receptor, there is a need for antagonists of this receptor as well. The nausea, abdominal cramping, and diarrhea which are associated with motilin agonsits are not always welcome physiological events. The increased gut motility induced by motilin has been implicated in diseases such as Irritable Bowel Syndrome and esophageal reflux. Therefore researchers have been searching for motilin antagonists.

One such antagonist is OHM-11526. This is a peptide derived from porcine motilin and competes with both motilin and erythromycin for the motilin receptor in a number of species, including rabbits and humans. In addition, this peptide is an antagonist of the contractile smooth muscle response to both erythromycin and motilin in an in vitro rabbit model. Depoortere, I. et al., *European Journal of Pharmacology*, 286, 241–47, (1995). Although this substance is potent in that model ($IC_{50}$ 1.0 nm) it is a peptide and as such offers little hope as an oral drug since it is susceptible to the enzymes of the digestive tract. Zen Itoh, *Motilin*, xvi (1990). Therefore it is desirable to find other agents which are not peptides as potential motilin antagonists. The compounds of this invention are such agents.

U.S. Pat. No. 5,972,939 to Chen et al. describes cyclopentene derivatives which are useful in treating gastrointestinal disorders associated with antagonizing the motilin receptor disorders. U.S. Pat. No. 5,972,939 doesn't disclose compounds of the present invention, in which $R_1$ is heteroarylaminocarbonyl optionally substituted with one or more $C_{1-5}$alkyl.

SUMMARY OF THE INVENTION

The present invention is directed to compounds of Formula I

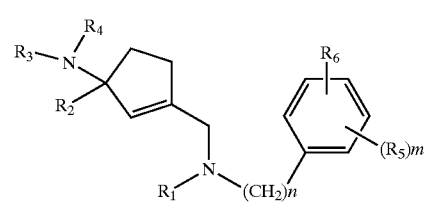

wherein $R_1$ is heteroarylaminocarbonyl optionally substituted with one or more $C_{1-5}$alkyl;

$R_2$ is selected from hydrogen, $C_{1-5}$alkyl, $C_{1-5}$alkoxy, phenyl optionally substituted with one or more substituents selected from the group consisting of halogen and $C_{1-5}$alkyl, and phenyl$C_{1-5}$alkyl optionally substituted with one or more substituents selected from the group consisting of halogen, $C_{1-5}$alkyl, $C_{1-5}$alkoxy, halo and di-$C_{1-5}$alkylamino;

$R_3$ is selected from hydrogen, $C_{1-5}$alkylcarbonyl optionally substituted with halogen, and phenylcarbonyl optionally substituted with one or more substituents selected from the group consisting of halogen, $C_{1-5}$alkyl, $C_{1-5}$alkoxy, amino, $C_{1-5}$alkylamino, and di-$C_{1-5}$alkylamino;

$R_4$ is selected from hydrogen, $C_{1-5}$alkyl, $C_{1-5}$alkylcarbonyl optionally substituted with halogen, and phenylcarbonyl optionally substituted with one or more substituents selected from the group consisting of halogen, $C_{1-5}$alkyl, $C_{1-5}$alkoxy, amino, $C_{1-5}$alkylamino, and di-$C_{1-5}$alkylamino;

n is 0–3;
m is 1–5;
$R_5$ is

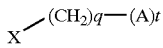

wherein:
q is 0–3;
t is 0–1;
X is oxygen, $CH_2$, sulfur, hydroxy, thiol, or $NR_c$ wherein
  $R_c$ is selected from hydrogen, $C_{1-5}$alkyl, morpholino$C_{1-5}$alkyl, piperidinyl$C_{1-5}$alkyl, N-phenylmethylpiperidinyl, and piperazinyl$C_{1-5}$alkyl,
with the proviso that if q and t are 0, X is hydroxy, thiol, or amino,
A is $C_{1-5}$alkoxycarbonyl, phenylcarbonyl, or $R_7R_8N$— wherein $R_7$ and $R_8$ are independently selected from hydrogen, $C_{1-5}$alkyl, and cyclo$C_{1-9}$alkyl, or $R_7$ and $R_8$ form a 5- or 6-membered heterocyclic ring with one or more heteroatoms selected from the group consisting of oxygen, nitrogen, sulfur, and sulfoxides and N-oxides thereof;
$R_6$ is selected from hydrogen, halogen, $C_{1-5}$alkoxy, $C_{1-5}$alkylamino, and di-$C_{1-5}$alkylamino; or a pharmaceutically acceptable salt thereof.

The compounds of Formula I are useful in treating gastrointestinal disorders associated with the motilin receptor. The compounds compete with erythromycin and motilin for the motilin receptor. In addition, the compounds are antagonists of the contractile smooth muscle response to those ligands.

The present invention also comprises pharmaceutical compositions containing one or more of the compounds of formula I as well as methods for the treatment of disorders related to the gastrointestinal system which are associated with the motilin receptor. Such diseases include Irritable Bowel Syndrome, esophageal reflux, and the gastrointestinal side effects of erythromycin.

DETAILED DESCRIPTION OF THE INVENTION

The terms used in describing the invention are commonly used and known to those skilled in the art. However, the terms that could have other meanings are defined. "Independently" means that when there are more than one substituent, the substituents may be different. The term "alkyl" refers to straight, cyclic and branched-chain alkyl groups and "alkoxy" refers O-alkyl where alkyl is as defined supra. The symbol "Ph" refers to phenyl. "Halogen" or "halo" means F, Cl, Br, and I. The term "fused bicyclic aromatic" includes fused aromatic rings such as naphthyl and the like. The term "fused bicyclic heterocycle" includes benzodioxoles and the like. The term "heteroaryl" as used herein, means a stable five- or six-memberd monocyclic aromatic ring system which consists of carbon atoms and from one to three heteroatoms selected from O, N, or S. The heteroaryl group may be attached at any heteroatom or carbon atom which results in the creation of a stable structure. Examples of heteroaryl groups include, but are not limited to, triazole, thiazole, thiadiazole, oxazole, imidazole, pyrazole, pyrimidine, isothiazole, isoindole, isoxazole and the like. The heteroaryl group may be substituted with one or more groups such as alkyl, substituted alkyl, and halogen. More particularly, the heteroaryl group may be substituted with methyl.

The term "subject" as used herein, refers to an animal, preferably a mammal, most preferably a human, who has been the object of treatment, observation or experiment.

Since the compounds of the invention have a chiral center, they may be prepared as a single stereoisomer or in racemic form as a mixture of some possible stereoisomers. The non-racemic forms may be obtained by either synthesis or resolution. The compounds may, for example, be resolved into their components enantiomers by standard techniques, such as the formation of diastereomeric pairs by salt formation. The compounds may also be resolved by covalent linkage to a chiral auxiliary, followed by chromatographic separation and/or crystallographic separation, and removal of the chiral auxiliary. Alternatively, the compounds may be resolved using chiral chromatography.

When compounds contain a basic moiety, acid addition salts may be prepared and may be chosen from hydrochloric, hydrobromic, hydroiodic, perchloric, sulfuric, nitric, phosphoric, acetic, propionic, glycolic, lactic, pyruvic, oxalic, malonic, succinic, maleic, fumaric, malic, tartaric, citric, benzoic, cinnamic, mandelic, methanesulfonic, p-toluenesulfonic, cyclohexanesulfamic, salicylic, 2-phenoxybenzoic, 2-acetoxybenzoic, or saccharin, and the like. Such salts can be made by reacting the free base of compounds of formula I with the acid and isolating the salt.

Intermediates of the present invention may be prepared by known methods such as those disclosed in U.S. Pat. No. 5,972,939 to Chen et al., which is hereby incorporated by reference in its entirety.

The compounds of the invention may be prepared by the following procedures. Schemes 1 and 2 show the preparation of the intermediates; Schemes 3 and 4 show the preparation of the compounds of the invention. Where compounds of the invention may be made by more than one scheme, the choice of scheme is a matter of discretion which is within the capabilities of those skilled in the art.

Essentially, Scheme 1 assembles two halves of the intermediate and couples them. For one-half, 3-ethoxy-2-cyclohexen-1-one, 1a (a known compound), may be the starting material. 1a may be treated with a Grignard reagent, 1b, such as 4-fluorobenzyl magnesium bromide (a known compound) preferably at room temperature (rt) under an inert atmosphere, using ether as a solvent to give the α,β-unsaturated ketone derivative 1c. Treatment of 1c with a reducing agent such as lithium aluminum hydride (LAH) preferably at 0° C. to room temperature gives the alcohol 1d. This alcohol may be treated with a strong base such as NaH and trichloroacetonitrile preferably from 0° C. to room temperature to give the amide 1e. This six-membered ring amide may be sequentially treated on dry ice with ozone, dimethylsulfide, and a catalytic amount of acid such as toluene sulfonic acid. Once addition is complete, the mixture may be warmed to room temperature to give the five-membered ring aldehyde 1f, as a racemic mixture.

To assemble the other half, an aromatic alcohol 1g, such as 3-hydroxyaniline may be treated with a mild base, such as $K_2CO_3$, in a suitable solvent such as ethanol (EtOH) at reflux. This mixture may be subsequently treated with a halide derivative 1h, such as 3-chloropropylmorpholine preferably at room temperature to give the amine 1i. This amine may be treated with the aldehyde 1f and $NaCNBH_3$ in methanol (MeOH) preferably at room temperature to give an intermediate 1j as a racemic mixture.

If pure enantiomers are desired, they may be obtained in any of three stages of the above synthesis. The intermediates 1d, 1f, and 1j may all be separated via HPLC using chiral columns or methods known of those skilled in the art. With respect to all three compounds, they may be further manipulated to give other compounds of the invention without sacrificing their enantiomeric purity.

Scheme 1 may be used to produce other intermediates that may be used to make other compounds of the invention. For example, to produce compounds where X is sulfur, simply replace reagent 1h with an aromatic thiol, such as 3-aminothiophenol and carry out the remaining steps of the Scheme.

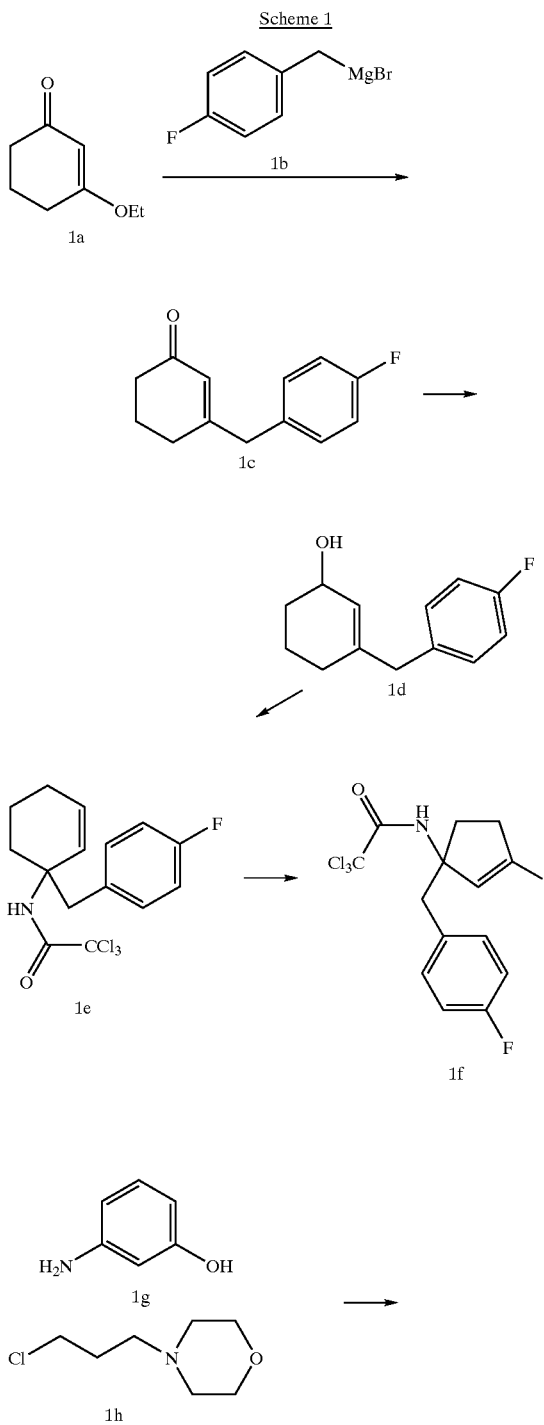

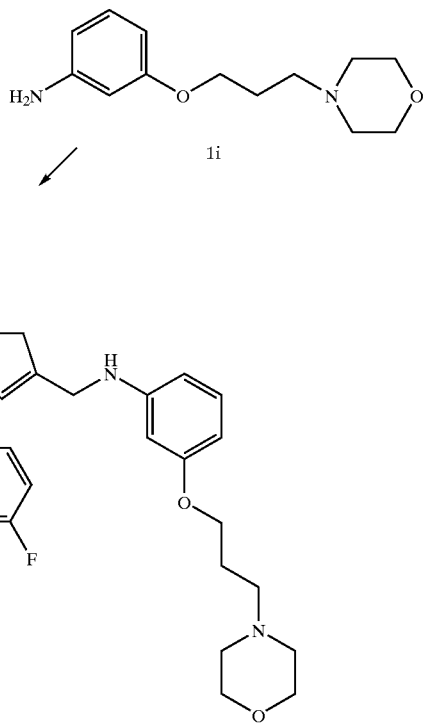

To produce other substitutions at $R_3$ or $R_4$, some of the products of Scheme 1 may be used as shown in Scheme 2. For example, to produce a compound where $R_3$ is hydrogen and $R_4$ is $CH_3C(O)$—, the six-membered ring intermediate 1e, may be treated with a base, such as barium hydroxide, at reflux in EtOH to give the free amine 2a. The amine may be subsequently treated with an acid anhydride such as trifluoroacetic anhydride to give 2b. This intermediate may be carried through the remaining steps of Scheme 1 to produce the desired intermediate.

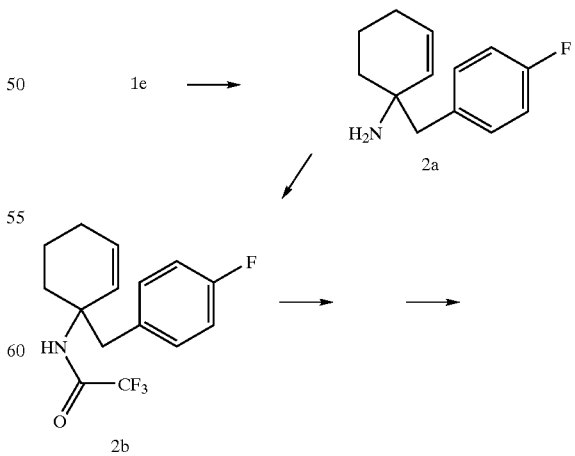

-continued

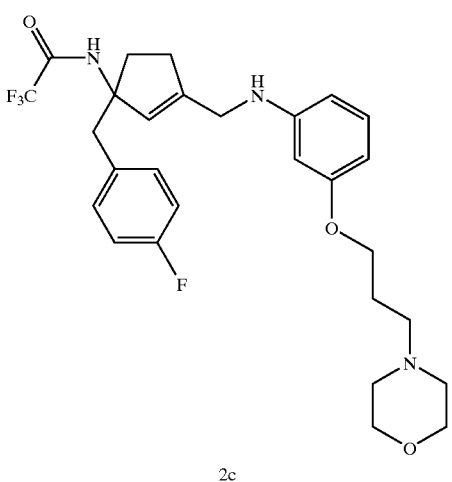

2c

As shown in Scheme 3, reaction of 1j with 4-nitrophenyl chloroformate (3b) and triethylamine in methylene chloride will yield the urethane derivative, 3c. Reaction of 3c with a heteroaryl amine (3d, such as 2-amino-1,3,4-thiadiazole, a known compound) will yield a compound of Formula 1b in THF or 1,4-dioxane at reflux temperature.

Scheme 3

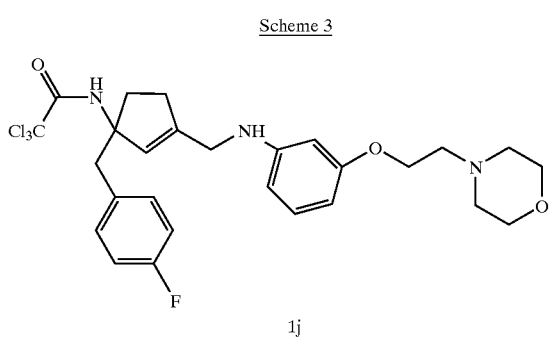

1j

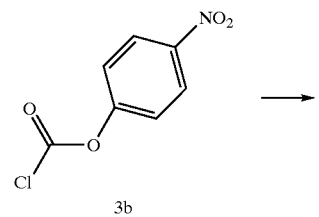

3b

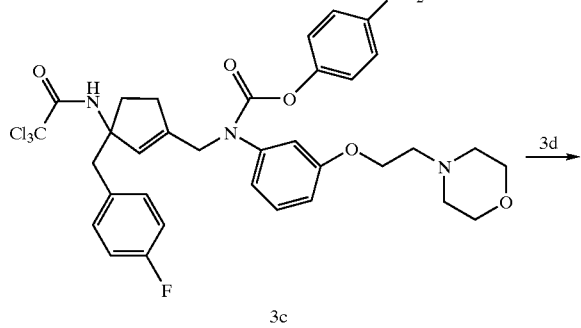

3c

-continued

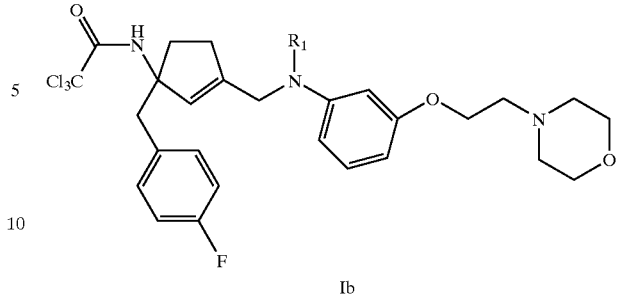

Ib

To produce compounds of the invention wherein $R_7$ and $R_8$ form sulfoxide or N-oxide, the procedure of Scheme 4 may be followed (MCPBA refers to 3-chloroperoxybenzoic acid).

Scheme 4

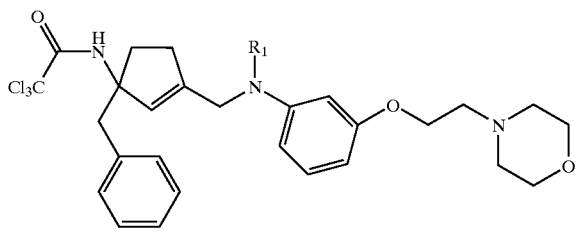

4a

| MCPBA
| CH$_2$Cl$_2$

4b

Radiolabeled Motilin

A compound of the invention was tested for its ability to compete with radiolabeled motilin (porcine) for the motilin receptors located on the colon of mature rabbits. The colon from mature New Zealand rabbits was removed, dissected free from the mucosa and serosa layers, and diced into small pieces. The muscle tissues were homogenized in 10 volumes of buffer (50 mM Tris-Cl 10 MM MgCl$_2$, 0.1 mg/mL bactracin, and 0.25 mM Peflabloc, pH 7.5) in a Polytron (29,000 rpm, 4×15 seconds). The homogenate was centrifuged at 1000×g for 15 min. and the supernatant discarded. The pellet was washed twice before being suspended in homogenizing buffer. This crude homogenate was then passed first through a 19 gauge needle then a 23 gauge needle to further suspend the material and stored at −80° C. In a total volume of 0.50 mL, the binding assay contained the following components added sequentially: buffer (50 mM Tris-Cl, 10 mM MgCl$_2$, 1 mM EDTA (ethylenediaminetetracetic acid), 15 mg/mL BSA (Bovine Serum Albumin), 5 μg/mL leupeptin, aprotinin, and pepstatin, and 0.1 mg/mL, bactracin), I$^{125}$ motilin (Amersham, ca 50,000–70,000 cpm, 25–40 pM), the test compound (the initial concentration was 2 mM/100% DMSO, which was diluted with H$_2$O to a final concentration of 10 μM) and membrane protein (100–300 μg). After 30 min, at 30° C., the material was cooled on ice and centrifuged at 13,000×g for 1 minute. The pellet was washed with 1 mL 0.9% saline and centrifuged at 13,000×g for 15 seconds. The pellet was washed again with cold saline and the supernatant was removed. The pellet was counted in the gamma counter to determine the percentage of unbound motilin and thereby the percent inhibition of the test compound.

% Inhibition was Determined by Standard Techniques

3-Benzyl-3-trichloroacetylamino—N-[(3-(2-morpholinoethoxy)phenyl)-N-[(1,3,4-thiadiazol-2-yl) aminocarbonyl)amino]methylcyclopentene (Example 2): 17% @100 nM.

Rabbit duo denum smooth muscle

Compounds of the invention may be evaluated for their ability to inhibit motilin and erythromycin induced contractions in the rabbit duodenum smooth muscle. Rabbits can be fasted 24–48 h and euthanized. The venral midline incision may be made approximately 7.5 cm above the umbilicus up to the xyphoid process, exposing the upper peritoneal cavity. The first 8 cm. of the duodenum starting at the pyloric valve may be quickly removed and placed in Krebs solution containing NaCl, (120 m), KCl (4.7 mM), MgSO$_4$*7H$_2$O (1.2 mM), CaCl$_2$*2H$_2$O (2.4 mM), KH$_2$PO$_4$ (1 mM), D-glucose (10 mM), and NaHCO$_3$ (24 mM). The lumen may be flushed with Krebs and excess tissue removed. The tissue may be cut lengthwise, splayed open with the longitudinal muscle layer facing up, and the longitudinal muscle layer released away from the circular muscle and cut into 3×30 mm strips. A pre-tied 4-0 silk ligature with a loop may be placed at the middle of the strip and the strip may be folded over the loop so the strip is half its original length. The tissues may be mounted in a 10 mL tissue bath (Radnotti Glass Technology, Inc., Monrovia, Calif.) containing Krebs solution gassed with 95% O$_2$ 5% CO$_2$ at 37° C. The tissues may be attached to a force displacement transducer (FT03, Grass Instruments, Quincy, Mass.) and resting tension slowly increased to 1 g. The tissues may be allowed to equilibrate for 60–90 min with 2–3 wash cycles. The tissues may be equilibrated with two initial contractions induced by a concentration of acetylcholine (1×10$^{-4}$ M) that produced a maximal contraction (0.1 mM), with the highest taken as 100% maximal contraction of that tissue. Base line and response levels are expressed as grams tension developed and as a percent of the response to acetylcholine. The test compounds may be dissolved in DMSO (2 mM/100% DMSO) and applied to the prepared strips 5–15 minutes prior to the addition of porcine motilin. After addition, the tension may be constantly monitored over 5 min and the maximum tension may be recorded. The percent contraction may be measured at four ascending concentrations and where appropriate IC$_{50}$'s may be determined.

The particularly preferred compounds are those where R$_1$ is heteroarylaminocarbonyl substituted with one or more methyl.

In another embodiment of the present invention:

R$_2$ is phenylC$_{1-5}$alkyl;
R$_3$ is C$_{1-5}$alkylcarbonyl substituted with halogen;
R$_4$ is hydrogen;
R$_6$ is hydrogen
n is 0;
m is 1 or 2;
q is 2;
t is 1;
X is oxygen; and
A is R$_7$R$_8$N— wherein R$_7$ and R$_8$ taken together form a 5- or 6-membered heterocyclic ring with one or more heteroatoms selected from the group consisting of oxygen, nitrogen, sulfur and N-oxides thereof.

In another example of a compound of Formula I:

R$_2$ is phenylC$_{1-5}$alky;
R$_3$ is C$_{1-5}$alkylcarbonyl substituted with halogen;
R$_4$ is hydrogen;
n is 0;
m is 2;
q is 2;
t is 1; and
X is oxygen;
A is R$_7$R$_8$N— wherein R$_7$ and R$_8$ are taken together to form a 5- or 6-membered heterocyclic ring with one or more heteroatoms selected from the group consisting of oxygen, nitrogen, sulfur, and N-oxides thereof.

Also illustrative of the present invention is the compound of Formula I wherein R$_3$ is trifluoromethylacetyl and R$_5$ is O—(CH$_2$)$_2$-morpholine-1-yl.

To prepare the pharmaceutical compositions of this invention, one or more compounds or salts thereof, as the active ingredient, is intimately admixed with a pharmaceutical carrier according to conventional pharmaceutical compounding techniques, which carrier may take a wide variety of forms depending on the form of preparation desired for administration, e.g., oral or parenteral. In preparing the compositions in oral dosage form, any of the usual pharmaceutical media may be employed. Thus for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage form, in which case solid pharmaceutical carriers are obviously employed. If desired, tablets may be sugar coated or enteric coated by standard techniques. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. The pharmaceutical compositions herein will preferably contain per dosage unit, e.g., tablet, capsule, powder, injection, teaspoonful and the like, from about 5 to about 500 mg of the active ingredient, although other unit dosages may be employed.

In therapeutic use for treating disorders of the gastrointestinal system in mammals, the compounds of this invention may be administered in an amount of from about 0.5 to 100 mg/kg 1–2 times per day orally. In addition the compounds may be administered via injection at 0.1–10 mg/kg per day. Determination of optimum dosages for a particular situation is within the capabilities of formulators.

In order to illustrate the invention, the following examples are included. These examples do not limit the invention. They are meant to illustrate and suggest a method of practicing the invention. Although there are other methods of practicing this invention, those methods are deemed to be within the scope of this invention.

EXAMPLES

Example 1

3-Benzyl-3-trichloroacetylamino—N-[(3-(2-morpholinoethoxy)phenyl)-N-(4-nitrophenoxycarbonyl)amino]methylcyclopentene To a solution of 3-benzyl-3-trichloroacetylamino—N-[(3-(2-morpholinoethoxy)phenyl)amino]methylcyclopentene (105 mg, 0.19 mM)), triethylamine (150 mg) in methylene chloride (30 mL) was added 4-nitrophenyl chloroformate (62 mg,) at room temperature under nitrogen and stirred for 2 hours. The resulting mixture was poured into ice water (30 mL). The organic layer was separated and the aqueous layer was extracted with methylene chloride (2×10 mL). The combined organic layer was dried and the solvent was removed in vacuo. The residue was purified by column chromatography on silica gel (ethyl acetate/hexane 9:1) to give the title compound as a thick yellow oil (113 mg, 82%); MS (MH$^+$=717).

Example 2

3-Benzyl-3-trichloroacetylamino—N-[(3-(2-morpholinoethoxy)phenyl)-N-[(1,3,4-thiadiazol-2-yl)aminocarbonyl)amino]methylcyclopentene A mixture of 3-benzyl-3-trichloroacetylamino-N-[(3-(2-morpholinoethoxy)phenyl)-N-(4-nitrophenoxycarbonyl) amino]methylcyclopentene (51 mg, 0.07 mM) and 2-amino-1,3,4-thiadiazole (25 mg, 0.25 mM) in xylene was heated to reflux under nitrogen for hours. The resulting mixture was cooled to room temperature and the solvent was removed in vacuo. The residue was purified by preparative TLC on silica gel to give the title compound as thick yellow oil (32 mg, 67%); MS (MH$^+$=679). This was converted into mono hydrochloride salt (pale yellow powder) in a usual manner.

What is claimed is:

1. A method of treating a disorder of the gastrointestinal system comprising administering to a subject an effective amount of a compound of Formula (I):

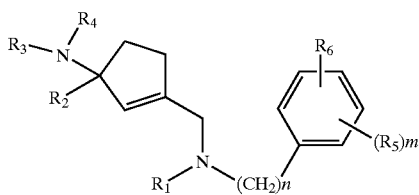

wherein
  $R_1$ is heteroarylaminocarbonyl optionally substituted with one or more $C_{1-5}$alkyl;
  $R_2$ is selected from hydrogen, $C_{1-5}$alkyl, $C_{1-5}$alkoxy, phenyl optionally substituted with one or more substituents selected from the group consisting of halogen and $C_{1-5}$alkyl, and phenyl$C_{1-5}$alkyl optionally substituted with one or more substituents selected from the group consisting of halogen, $C_{1-5}$alkyl, $C_{1-5}$alkoxy, halo and di-$C_{1-5}$alkylamino;
  $R_3$ is selected from hydrogen, $C_{1-5}$alkylcarbonyl optionally substituted with halogen, and phenylcarbonyl optionally substituted with one or more substituents selected from the group consisting of halogen, $C_{1-5}$alkyl, $C_{1-5}$alkoxy, amino, $C_{1-5}$alkylamino, and di-$C_{1-5}$alkylamino;
  $R_4$ is selected from hydrogen, $C_{1-5}$alkyl, $C_{1-5}$alkylcarbonyl optionally substituted with halogen, and phenylcarbonyl optionally substituted with one or more substituents selected from the group consisting of halogen, $C_{1-5}$alkyl, $C_{1-5}$alkoxy, amino, $C_{1-5}$alkylamino, and di-$C_{1-5}$alkylamino;
  n is 0–3;
  m is 1–5;
  $R_5$ is

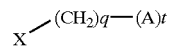

wherein:
  q is 0–3;
  t is 0–1;
  X is oxygen, $CH_2$, sulfur, hydroxy, thiol, or $NR_c$ wherein
    $R_c$ is selected from hydrogen, $C_{1-5}$alkyl, morpholino$C_{1-5}$alkyl, piperidinyl$C_{1-5}$alkyl, N-phenylmethylpiperidinyl, and piperazinyl$C_{1-5}$alkyl,
  with the proviso that if q and t are 0, X is hydroxy, thiol, or amino,
  A is $C_{1-5}$alkoxycarbonyl, phenylcarbonyl, or $R_7R_8N$— wherein $R_7$ and $R_8$ are independently selected from hydrogen, $C_{1-5}$alkyl, and cyclo$C_{1-9}$alkyl, or $R_7$ and $R_8$ form a 5- or 6-membered heterocyclic ring with one or more heteroatoms selected from the group consisting of oxygen, nitrogen, sulfur, and sulfoxides and N-oxides thereof;
  $R_6$ is selected from hydrogen, halogen, $C_{1-5}$alkoxy, $C_{1-5}$alkylamino, and di-$C_{1-5}$alkylamino;
or a pharmaceutically acceptable salt thereof.

2. A method of claim 1, wherein the condition is irritable bowel syndrome or esophageal reflux.

3. A method of claim 1, wherein the compound is a compound of Formula (I):

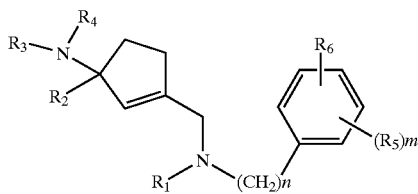

wherein
  $R_2$ is phenyl$C_{1-5}$alkyl;
  $R_3$ is $C_{1-5}$alkylcarbonyl substituted with halogen;
  $R_4$ is hydrogen;
  $R_6$ is hydrogen
  n is 0;
  m is 1 or 2;
  q is 2;
  t is 1;
  X is oxygen; and
  A is $R_7R_8N$— wherein $R_7$ and $R_8$ taken together form a 5- or 6-membered heterocyclic ring with one or more heteroatoms selected from the group consisting of oxygen, nitrogen, sulfur and N-oxides thereof.

4. A method of claim 3, wherein the compound is a compound of Formula (I):

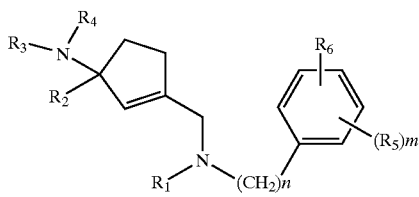

wherein $R_3$ is trifluoromethylacetyl and $R_5$ is O—$(CH_2)_2$-morpholine-1-yl.

5. A method of claim 1, wherein the compound is a compound of Formula (Ia):

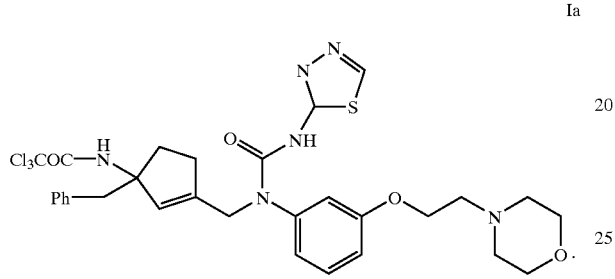

6. A method of treating a gastrointestinal side effect resulting from administration of erythromycin, which comprises administering to a subject an effective amount of a compound Formula I:

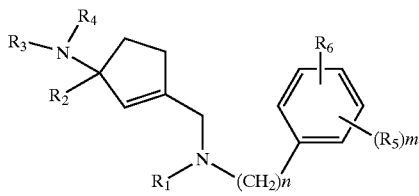

wherein $R_1$ is heteroarylaminocarbonyl optionally substituted with one or more $C_{1-5}$alkyl;

$R_2$ is selected from hydrogen, $C_{1-5}$alkyl, $C_{1-5}$alkoxy, phenyl optionally substituted with one or more substituents selected from the group consisting of halogen and $C_{1-5}$alkyl, and phenyl$C_{1-5}$alkyl optionally substituted with one or more substituents selected from the group consisting of halogen, $C_{1-5}$alkyl, $C_{1-5}$alkoxy, halo and di-$C_{1-5}$alkylamino;

$R_3$ is selected from hydrogen, $C_{1-5}$alkylcarbonyl optionally substituted with halogen, and phenylcarbonyl optionally substituted with one or more substituents selected from the group consisting of halogen, $C_{1-5}$alkyl, $C_{1-5}$alkoxy, amino, $C_{1-5}$alkylamino, and di-$C_{1-5}$alkylamino;

$R_4$ is selected from hydrogen, $C_{1-5}$alkyl, $C_{1-5}$alkylcarbonyl optionally substituted with halogen, and phenylcarbonyl optionally substituted with one or more substituents selected from the group consisting of halogen, $C_{1-5}$alkyl, $C_{1-5}$alkoxy, amino, $C_{1-5}$alkylamino, and di-$C_{1-5}$alkylamino;

n is 0–3;

m is 1–5;

$R_5$ is

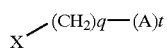

wherein:

q is 0–3;

t is 0–1;

X is oxygen, $CH_2$, sulfur, hydroxy, thiol, or $NR_c$ wherein $R_c$ is selected from hydrogen, $C_{1-5}$alkyl, morpholino$C_{1-5}$alkyl, piperidinyl$C_{1-5}$alkyl, N-phenylmethylpiperidinyl, and piperazinyl$C_{1-5}$alkyl, with the proviso that if q and t are 0, X is hydroxy, thiol, or amino, A is $C_{1-5}$alkoxycarbonyl, phenylcarbonyl, or $R_7R_8N$— wherein $R_7$ and $R_8$ are independently selected from hydrogen, $C_{1-5}$alkyl, and cyclo$C_{1-9}$alkyl, or $R_7$ and $R_8$ form a 5- or 6-membered heterocyclic ring with one or more heteroatoms selected from the group consisting of oxygen, nitrogen, sulfur, and sulfoxides and N-oxides thereof;

$R_6$ is selected from hydrogen, halogen, $C_{1-5}$alkoxy, $C_{1-5}$alkylamino, and di-$C_{1-5}$alkylamino;

or a pharmaceutically acceptable salt thereof.

7. A method of claim 6, wherein the condition is irritable bowel syndrome or esophageal reflux.

8. A method of claim 6, wherein the compound is a compound of Formula (I):

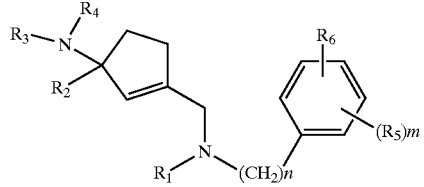

wherein $R_2$ is phenyl$C_{1-5}$alkyl;

$R_3$ is $C_{1-5}$alkylcarbonyl substituted with halogen;

$R_4$ is hydrogen;

$R_6$ is hydrogen n is 0;

m is 1 or 2;

q is 2;

t is 1;

X is oxygen; and

A is $R_7R_8N$— wherein $R_7$ and $R_8$ taken together form a 5- or 6-membered heterocyclic ring with one or more heteroatoms selected from the group consisting of oxygen, nitrogen, sulfur and N-oxides thereof.

9. A method of claim 6, wherein the compound is a compound of Formula (I):

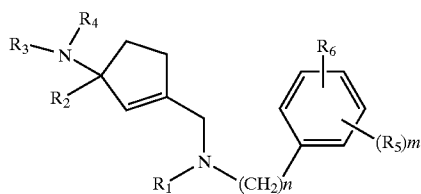

wherein R₃ is trifluoromethylacetyl and R₅ is O—(CH₂)₂-morpholine-1-yl.

10. A method of claim 6, wherein the compound is a compound of Formula (Ia):

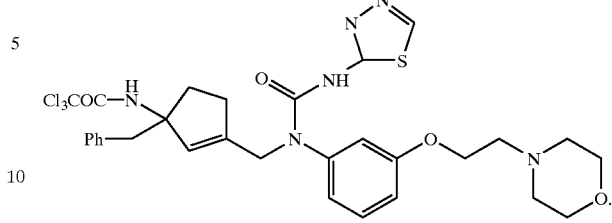

11. A method of claim 1 wherein said disorder of the gastrointestinal system is selected from gastrointestinal emptying, chronic idiopathic intestinal pseudo-obstruction, gastroparesis, irritable bowel syndrome, esophageal reflux, nausea, abdominal cramping and diarrhea.

* * * * *